United States Patent
Osborne et al.

(12) 
(10) Patent No.: US 6,716,441 B1
(45) Date of Patent: Apr. 6, 2004

(54) COMPOSITIONS FOR EFFICIENT RELEASE OF ACTIVE INGREDIENTS

(75) Inventors: Scott Edward Osborne, Middletown, OH (US); George Endel Deckner, Cincinnati, OH (US); Thomas James Klofta, Cincinnati, OH (US); Victor Nicholas Vega, Cincinnati, OH (US)

(73) Assignee: The Procter & Gamble Company, Cincinnati, OH (US)

(*) Notice: Subject to any disclaimer, the term of this patent is extended or adjusted under 35 U.S.C. 154(b) by 0 days.

(21) Appl. No.: 09/466,343

(22) Filed: Dec. 17, 1999

Related U.S. Application Data

(63) Continuation-in-part of application No. 09/041,266, filed on Mar. 3, 1998, now abandoned.

(51) Int. Cl.$^7$ .......................... A01N 25/34; A61K 9/00
(52) U.S. Cl. .................. 424/404; 424/400; 424/443; 424/444; 424/447; 424/449; 424/445; 424/446; 424/70.11; 604/385; 604/368; 604/378; 514/946; 514/947
(58) Field of Search ................ 424/404, 407, 424/443, 444, 445, 446, 447, 449, 70.31, 70.11, 400; 514/946, 947; 604/363, 385, 378

(56) References Cited

U.S. PATENT DOCUMENTS

| | | |
|---|---|---|
| 2,804,424 A | 8/1957 | Stirn et al. |
| 3,489,148 A | 1/1970 | Duncan et al. |
| 3,490,454 A | 1/1970 | Goldfarb et al. |
| 3,585,998 A | 6/1971 | Hayford et al. |
| 3,875,942 A | 4/1975 | Roberts et al. |
| 3,896,807 A | 7/1975 | Buchalter |
| 3,902,493 A | 9/1975 | Baier et al. |
| 4,112,167 A | 9/1978 | Dake et al. |
| 4,263,363 A | 4/1981 | Buck et al. |
| 4,324,247 A | 4/1982 | Aziz |
| 4,513,051 A | 4/1985 | Lavash |
| 4,556,560 A | 12/1985 | Buckingham |
| 4,563,346 A | 1/1986 | Deckner ................ 424/59 |
| 4,569,343 A | 2/1986 | Kimura et al. |
| 4,623,339 A | 11/1986 | Ciraldo et al. |
| 4,666,765 A | 5/1987 | Caldwell et al. |
| 4,695,452 A | 9/1987 | Gannis et al. ............. 424/59 |
| 4,704,112 A | 11/1987 | Suzuki et al. |
| 4,753,643 A | 6/1988 | Kassai |
| 4,790,836 A | 12/1988 | Brecher |
| 4,882,204 A | 11/1989 | Tenenbaum |
| 4,900,317 A | 2/1990 | Buell |
| 4,904,524 A | 2/1990 | Yoh |
| 4,919,934 A * | 4/1990 | Deckner et al. .......... 424/401 |
| 4,959,059 A | 9/1990 | Eilender et al. |
| 4,990,144 A | 2/1991 | Blott |
| 4,996,238 A | 2/1991 | Matravers |
| 4,996,239 A | 2/1991 | Matravers ............... 514/873 |
| 5,043,155 A | 8/1991 | Puchalski et al. ......... 424/78 |
| 5,194,261 A | 3/1993 | Pichierri |
| 5,264,460 A | 11/1993 | Jakobson et al. |
| 5,321,098 A | 6/1994 | Lal |
| 5,370,132 A | 12/1994 | Weber et al. |
| 5,415,649 A | 5/1995 | Watanabe et al. |
| 5,444,096 A | 8/1995 | McCrea et al. ............. 514/770 |
| 5,509,915 A | 4/1996 | Hanson et al. |
| 5,525,346 A | 6/1996 | Hartung et al. |
| 5,558,655 A | 9/1996 | Jezzi et al. |
| 5,609,587 A | 3/1997 | Roe |
| 5,614,178 A | 3/1997 | Bloom et al. ............. 424/60 |
| 5,618,529 A | 4/1997 | Pichierri |
| 5,635,191 A | 6/1997 | Roe et al. |
| 5,643,588 A | 7/1997 | Roe et al. |
| 5,665,364 A | 9/1997 | McAtee et al. ............ 424/401 |
| 5,733,534 A * | 3/1998 | Sawin et al. ............. 424/65 |
| 5,763,497 A | 6/1998 | Ikeda et al. ............. 514/943 |
| 5,843,411 A * | 12/1998 | Hernandez et al. ......... 424/59 |
| 6,153,209 A | 11/2000 | Vega et al. ............. 424/404 |

FOREIGN PATENT DOCUMENTS

| | | |
|---|---|---|
| CA | 2019557 | 12/1990 |
| DE | 4136540 A1 | 5/1992 |
| DE | 198 52 196 A1 | 5/2000 |
| EP | 0 297 828 A1 | 1/1989 |
| EP | 0 631 768 A1 | 1/1995 |
| EP | 0 631 774 A1 | 1/1995 |
| EP | 0 692 263 A3 | 1/1996 |
| EP | 0 804 923 A2 | 11/1997 |
| EP | 1 080 713 A2 | 3/2001 |
| GB | 2033751 A | 5/1980 |
| JP | 61-028078 | 2/1986 |
| JP | 02-31756 | 2/1990 |
| JP | 05-285170 | 11/1993 |
| JP | 08-52175 | 2/1996 |
| WO | WO 88/04168 | 6/1988 |
| WO | WO 96/27364 | 9/1996 |
| WO | WO 99/13861 | 3/1999 |
| WO | WO 99/45973 | 9/1999 |
| WO | WO 99/45976 | 9/1999 |
| WO | WO 00/67728 A2 | 11/2000 |

OTHER PUBLICATIONS

Product Information—Copies of Front and Back of Johnson's Diaper Rash Ointment box.

* cited by examiner

*Primary Examiner*—Thurman K. Page
*Assistant Examiner*—Lakshmi Channavajjala
(74) *Attorney, Agent, or Firm*—Caroline H. Wei-Berk; Eileen L. Hughett; Eric T. Addington

(57) ABSTRACT

The present invention relates to a novel composition for efficiently releasing hydrophilic or water-soluble skin care actives from an oleaginous composition. The substantially oleaginous composition of the present invention comprises: (1) at least one skin care active; (2) a release agent having an HLB of at least about 3; and (3) a hydrophobic barrier protectant. The novel release composition may be topically applied to skin using a dispensing means such as an absorbent article, a wipe, a bandage, a pad, a canister, a stick, an aerosol dispenser, a sprayer, and the like.

12 Claims, No Drawings

COMPOSITIONS FOR EFFICIENT RELEASE OF ACTIVE INGREDIENTS

This is a continuation-in-part of application Ser. No. 09/041,266, filed on Mar. 3, 1998, now abandoned.

BACKGROUND OF THE INVENTION

The present invention relates to the effective delivery of a therapeutic skin care active to the skin via a novel release composition which is preferably incorporated into a dispensing means. Many types of disposable absorbent articles, such as diapers, training pants, adult incontinence devices, sanitary napkins, panty liners, and the like are available to absorb and contain urine and other bodily exudates. Disposal products of this type generally comprise some sort of liquid-pervious topsheet material, an absorbent core, and a liquid-impervious backsheet material. While these absorbent articles are efficient for the absorption of liquids, they also create a more hostile environment than that is usually encountered by the skin, increasing the risk of skin irritations and/or diaper dermatitis. Diaper dermatitis or diaper rash is a condition where the stratum corneum is attacked and the skin is irritated and inflamed. The commonly known factors linked to diaper dermatitis include ammonia, bacteria, the products of bacterial actions, enzymes, pH, candida albicans and moisture. The diaper dermatitis is principally initiated by prolonged and repeated exposure to urine and feces under occlusive condition such as the micro-environment created by wearing an absorbent article. Under such condition, the skin may get overhydrated, leading to diminished barrier function. The friction and rubbing with the absorbent article create further damages to the skin. Thus, the skin becomes more susceptible to the irritants such as those in the urine or feces. While this condition is certainly more common in infants, it is not limited to infants. Similar conditions occur in, for example, incontinent or bed-ridden adults. Furthermore, similar skin irritation may occur from use of sanitary napkins and from repeated wiping/chaffing of sensitive skin.

Since there are multiple factors linked to diaper dermatitis, the practical approach attempts to address the multiple causes and/or important cofactors. For example, reducing skin hydration by frequent changing of diapers, the use of moisture absorbing powders, the use of superabsorbent materials, and improving air flow in diapers are well known approaches. The use of artificial barriers (e.g., ointments, lotions) is also widely practiced.

Typically, a topical cream, ointment, lotion or paste is applied to the skin under the absorbent article by hand to provide some degree of physical barrier protection against bodily exudates or irritants. For the topical application method to be effective, the creams or ointments need to be substantive, i.e., they need to coat the target surface and remain at the site of application. Most current topical delivery systems are O/W or W/O (oil in water or water in oil) emulsions. These emulsions generally have inferior substantive properties, hence they are easily removed by moisture (from washing, perspiration or other bodily exudates), or rubbing against clothing, and often fail to provide long-lasting benefits to the site of application. These water-containing emulsions are particularly unsuitable for overhydrated skin such as is under an absorbent article. Water-free creams or ointments are also known. Typically, these creams or ointments use oleaginous base such as petrolatum to provide the substantively of the creams or ointments for a long-lasting coating of the target areas.

In another approach, multi-ingredients lotion compositions are used. Various active ingredients have been incorporated into topically applied compositions to treat or prevent diaper rash caused by the prolonged contact of skin with bodily exudates. For example, to combat the irritants and protect or enhance the skin's barrier properties, a host of cosmetic or therapeutic skin care actives can be incorporated into a carrier and applied to the skin, either by hand or via a dispensing means. These active ingredients include barrier substances (such as zinc oxide), skin conditioning agents (such as lanolin), pH buffer substances, protease and/or enzyme inhibitors, and other active ingredients. Because these active ingredients are typically simple, low molecular weight compounds or mixtures, they are generally not applied alone, but in combination with a carrier system. Most typical carrier systems are emulsions having a water phase and an oil phase, such as O/W or W/O emulsions. Less common delivery systems are substantially anhydrous, oleaginous compositions. The oleaginous compositions are generally more substantive than the O/W or W/O emulsions; thus, they may serve as reservoirs from which the active ingredients are continuously delivered. However, they may not be efficient in delivering the active ingredients. This is so because many of the skin care actives are water-soluble or hydrophilic; thus, they exist as solid particles or powders in the oleaginous composition. These solid particles or powders are entrapped in the substantially anhydrous oleaginous base and cannot be easily released from the composition to the target skin surface. Moreover, even when these active ingredients are in contact with the target skin surface, they may not function efficiently in their solid form.

Therefore, it is desirable to have a substantive, non-irritating oleaginous composition that efficiently delivers water-soluble or hydrophilic skin care actives to the skin surface in their active form, which readily provide benefits to the skin. It is further desirable to provide an oleaginous composition from which the water-soluble or hydrophilic active is released more efficiently in its active form.

Moreover, it is desirable that the composition provides continuous and controlled release of the water-soluble or hydrophilic skin care actives from the oleaginous carrier system.

It is further desirable that in a preferred embodiment, this novel composition can be administered to the target skin area via multiple dispensing means, such as pads, bandages, patches, sticks, aerosol dispensers, pump sprays, trigger sprays, canisters, and absorbent articles. In this embodiment, it is desirable that the novel composition can be administered to the target skin without leaving a messy aesthetically unpleasing residue on the skin and without direct contact with the users' or applicators' hands, thus avoiding leaving a messy residue on the user's hands or requiring an additional cleaning step after administering the composition.

SUMMARY OF THE INVENTION

The present invention relates to a novel composition for efficiently releasing hydrophilic or water-soluble skin care actives from anoleaginous composition. Specifically, a hydrophilic-oleophilic release agent is incorporated into the novel composition to attract/absorb moisture which dissolve or solubilize the actives, and preferentially release the actives from the substantially oleaginous composition in their active forms.

A barrier protectant is also incorporated into the novel composition of the present invention. The barrier protectant, which serves as a substantially anhydrous carrier for the skin care actives and the release agent, is substantive. That is, it has a good staying power on the skin surface. It thus provides a coating over the skin to protect the skin against direct contact with bodily exudates, and against penetration by moisture or irritants that may result in skin irritation, inflammation, erythema, and other undesirable side effects. The barrier protectant coating also protects the skin against overhydration. Because of the good staying power of the barrier protectant on the skin surface, it may serve as a reservoir for continuous release of the skin care actives, and provide long-lasting skin benefits.

In one embodiment, the oleaginous composition of the present invention comprises: (1) at least one water-soluble skin care active; (2) a release agent having an HLB of at least about 3, preferably a nonionic surfactant, or a polymeric surfactant; and (3) a hydrophobic barrier protectant.

The novel composition of the present invention is suitable for topical application to the target skin surface via various dispensing means, such as canisters, sticks, aerosol dispensers, and web substrates including pads, bandages, wipes, absorbent articles, and the like. The composition is preferably at least semi-solid or solid at room temperature (about 20° C.); thus, it may be easily transferred to the skin via contact, shear, pressure, frictional or wear motions, body heat and combinations thereof. The semi-solid or solid consistency is also useful in locking/immobilizing the composition on the surface of the web substrate or retaining the composition within the dispensing means, when not in use.

In another embodiment, the composition further comprises emollients which supple, smooth, soften, coat and lubricate the skin. The emollient may also soften the composition such that is has a semi-solid to solid consistency suitable for topical application via dispensing means.

DETAILED DESCRIPTION OF THE INVENTION

Definitions

As used herein, the term "comprising" means that the various components, ingredients, or steps can be conjointly employed in practicing the present invention. Accordingly, the term "comprising" encompasses the more restrictive terms "consisting essentially of" and "consisting of".

As used herein, the phrase "dispensing means" refers to a web substrate or a container that incorporates the release composition, and when said web substrate or container is applied to a target skin surface, the release composition is at least partially transferable to the target skin surface via contact, shear, pressure, body heat, frictional or wear motions, and combinations thereof. The target surface may be the human skin in general, particularly the occluded human skin (i.e., skin located in areas generally under an occluded environment). Examples of appropriate dispensing means are disclosed below.

As used herein, the phrase "absorbent article" means diapers, training pants, sanitary napkins, pantyliners, incontinence pads, and the like.

As used herein the term "occluded skin" means skin located in areas generally in an occluded, and/or high humidity local environment, such as the skin under an absorbent article when the article is worn. However, the present invention is also useful for "compromised skin" which is not limited to a particular area of the body. As used herein, the term "compromised skin" means skin that has been subjected to repeated or chronic exposures, or one or more acute episodes of exposure, to bodily exudates (e.g., urine, feces, blood, sweat), moisture, irritants, etc. such that the skin develops redness, chaffing, roughness, wrinkled appearance or itchiness.

As used herein, the term "semi-solid" means that the release composition has a rheology typical of pseudoplastic or plastic liquids. When no shear is applied, the compositions can have the appearance of a semi-solid but can be made to flow as the shear rate is increased. Not intending to be bound by theory, it is believed that such compositions contain primarily solid components, as well as some liquid components at room temperature.

Other terms are defined herein where initially discussed.

All percentages, ratios and proportions used herein are by weight unless otherwise specified.

1. The Release Compositions

The release composition of the present invention provides a means of delivering skin care actives to the skin from an oil-based composition. The release composition is uniquely suited for releasing water-soluble actives, which generally exist as entrapped particles or powders in the oleaginous composition.

A release composition suitable for the present invention comprises one or more skin care actives, a release agent and a barrier protectant. The composition may be solid or semi-solid, at room temperature, such that it is substantially immobilized on or contained within the dispensing means. The composition may optionally comprise low melting emollients such that the resultant composition may become more readily transferable to the skin surface.

Without being bound by theory, it is believed that the release agent preferentially absorbs or attracts moisture to create a microenvironment within the substantially oleaginous composition such that the skin care actives, specifically the water-soluble ones, are at least partially solubilized. As such, the solubilized actives are preferentially released from the oleaginous matrix to the skin surface. Moreover, with more efficient release of the skin care active through the use of release agent, a lower concentration of actives is needed to achieve the desired skin care benefits. The preferential release coupled with the delivery of the skin care actives in their active form provide a surprisingly effective means of administering the actives such that a very small amount (at a level as low as $10^{-4}$ wt %) of actives in the composition is sufficient to achieve observable skin benefits.

Because of the propensity of the release agent to attract or absorb moisture, the release composition also comprises an effective barrier protectant to protect the skin from overhydration as well as direct contact with irritants such as urine, feces, blood, and the like. Overall, the composition has achieved an important balance between the moisture being drawn into the oleaginous release composition for preferential release of the actives, and the protection exposure of skin susceptible to overhydration problem, e.g., the occluded skin under an absorbent article. The barrier protectants useful herein are substantive. That is, when the release composition is applied to the skin, it remains on the skin surface as a long-lasting coating such that the barrier protectant and other chemicals in the compositions do not penetrate the surface layer of the skin and possibly cause irritation to the skin. Additionally, the long-lasting coating functions like a reservoir from which the skin care actives may be continuously released.

The composition is at least semi-solid or solid at room temperature, and it should have the melting/rheological profile such that it is readily transferable to the skin via contact, shear, pressure, frictional or wear motions, body heat and combinations thereof. It is found that emollients can optionally be incorporated to adjust the rheological properties of the release composition.

The semi-solid or solid consistency of the composition further provides the advantage of "locking" or localizing the composition on specific locations on the substrate-type dispensing means and minimizing migration to undesirable locations (e.g., absorbent cores, adhesives) where it may interfere with the performance of the substrate. The semi-solid or solid consistency of the composition is also preferred to retain the composition in the canister or stick type dispensing means when not in use. In one embodiment, the composition may have a liquid or viscous fluid consistency for a particular type of dispensing means such as that disclosed in co-pending U.S. patent application Ser. No. 09/370,396, filed on Aug. 6, 1999 by McOsker et al., which is incorporated by reference herein.

a. The Skin Care Actives

A wide variety of topically effective skin care actives can be incorporated into the release compositions of the present invention.

The skin care actives suitable for use in the present invention are hydrophilic or water-soluble. The term "water-soluble" as used herein means the skin care active has a solubility of at least 0.1 gram, preferably at least 1 gram, more preferably at least 3 grams, and most preferably at least 5 grams, in 100 grams of water at 25° C.

Skin care actives suitable for use herein include, but are not limited to skin conditioning agents, pH control agents, protease and/or enzyme inhibitors, anti-coenzymes, chelating agents, antibodies, antimicrobials, humectants, vitamins, skin protectants and/or skin soothing agents which meet the requisite aforementioned solubility in water.

Examples of suitable skin protectants include but are not limited to allantoin, aluminum hydroxide gel, calamine, cysteine hydrochloride, dexpanthenol, racemic methionine, sodium bicarbonate, and the like. Examples of suitable vitamins include but are not limited to Vitamins $B_3$, $B_5$, niacinamide, panthenol, Vitamin C and derivatives, and mixtures thereof. Proton donating agents or pH control agents useful herein may neutralize the alkalinity and lower or control the enzyme activities in the bodily exudates or irritants. Such pH control agents useful herein include but are not limited to citric acid, polyacrylic acid, and triacetin hydrolysate. Useful protease inhibitors, which control or reduce protease activities in bodily exudates or irritants, include but are not limited to serine proteases, metalloproteases, cysteine proteases, aspartyl proteases and peptidases, and phenylsulfonyl fluorides are particularly useful herein. Useful enzyme inhibitors, which control or reduce specific enzymatic activities of enzymes commonly found in bodily exudates or irritants include but are not limited to lipases, esterases, diesterases, ureases, amylases, elastases and nucleases. Chelating agents useful herein include but are not limited to ethylenediamine tetraacetic acid (EDTA) and its salts, ethylene diamine, triethanol amine and phytic acid, which bind to metal cofactors of specific enzymes. Anti-microbials useful in controlling or reducing microbial activities and derivatives, and antibodies which bind or control specific enzymes or proteases include but are not limited to hexamidine and its salts and derivatives, such as hexamidine diisethionate, pentamidine and its salts and derivatives, benzamidine and its salts and derivatives, and guanadinobenzoic acid and its salts and derivatives. Additionally, other nonlimiting examples of skin care actives useful herein are those water soluble skin care actives described in co-pending U.S. application Ser. No. 09/041,509, now abandoned, by McOsker et al. filed on Mar. 12, 1998; U.S. application Ser. No. 09/041,232, now abandoned, by Rourke et al filed on Mar. 12 1998; U.S. application Ser. No. 09/041,266, now abandoned, by Roe et al. and U.S. application Ser. No. 09/041,196, now U.S. Pat. No. 6,066,673, by Underiner et al., both filed on Mar. 12, 1998; Patent Application EP 97/120,699 and EP 97/120,700 both by Polumbo et al. and filed on Nov. 26, 1997; U.S. Pat. No. 5,091,193 issued to Enjolras et al, on Feb. 25, 1992; U.S. Pat. No. 4,556,560 issued to Buckingham on Dec. 3, 1985; U.S. Pat. No. 5,376,655 issued to Imaki et al. on Dec. 27, 1994; U.S. Pat. No. 5,376,655 issued to Imaki et al. on Dec. 27, 1994; U.S. Pat. No. 3,935,862 issued to Kraskin on Feb. 3, 1976; U.S. Pat. No. 5,409,903 issued to Polak et al. on Apr. 25, 1995; U.S. Pat. No. 4,556,560 issued to Buckingham on Dec. 3, 1985; all are incorporated by reference herein.

The skin care actives in the present invention should preferably include at least one of the following: allantoin, hexamidine and its salts and derivatives, such as hexamidine diisethionate, triacetin, phytic acid, ethylenediamine tetraacetic acid (EDTA), phenylsulfonyl fluorides such as 4-(2-aminoethyl)-benzenesulfonylfluoride hydrochloride, chitosan, and mixtures thereof.

The skin care actives are typically incorporated into the substantially oleaginous composition as micronized powder; conventional size particulates are less preferred due to the abrasive effect on the skin. As used herein, the "micronized powder" refers to particles having sizes (mean particle diameter and particle size distribution) that are below the tactile threshold and are essentially nonabrasive to the skin, and the "conventional size particles" refers to particles that are tactilely perceptible and provide the scrubbing and abrasive effects. Moreover, it is more difficult to form uniform and stable suspension using large particles in the substantially oleaginous composition of the present invention. Generally, particles having a mean particle diameter greater than about 75 microns are tactilely perceived; thus, the active particles should preferably have their size reduced prior to being incorporated herein. Particles having a wide range of shapes, surface characteristics, and hardness can be used herein, provided the size requirement is met.

Alternatively, the skin care actives may be solubilized in a small amount of water or water-miscible solvents such as lower alcohols, or glycols in the form of a solution, a suspension, a dispersion, an emulsion or the like, which is incorporated into the substantially oleaginous composition. Additionally, the skin care actives may also be incorporated in another structure that in turn is incorporated into the composition during manufacture or assembly. For example, the skin care active may be coated onto or otherwise attached or bound to a nanophase particulate structure or other solid support such as glass, plastic or agarose beads, and the like, or contained in pressure-rupturable or dissolvable microcapsules and the like. The use of other types of incorporatable elements for containing the skin care actives and methods for their incorporation will be readily apparent to one skilled in the art.

The release composition typically comprises from about $10^{-4}\%$ to about 20%, preferably about $10^{-3}\%$ to about 10%, and more preferably about $10^{-2}\%$ to about 3%, by weight of the release composition.

b. The Release Agents

Preferably, the release agent is substantially miscible with the oleaginous barrier protectant or other matrix materials to form a substantially uniform composition. To that end, the release agent should preferably be oleophilic. The release agent should also have some degree of hydrophilicity in order to attract/absorb moisture. Since the release agent is preferably both oleophilic and hydrophilic, it may microemulsify the substantially oleaginous composition when the composition is exposed to moisture. Microemulsification occurs on a localized level and may not rise to the level of total emulsification of the composition. Typically, the moisture may be provided by moisture in the atmosphere (e.g., the occluded local environment), or even bodily discharges, such as urine, runny feces, blood, perspiration or other bodily discharge.

In the absence of the release agent, the skin care actives are dispersed and entrapped in the oleaginous composition with little mobility. Application of pressure or shear action may allow the skin care actives to be released from the composition. Additionally, body heat may lower the viscosity of the composition which facilitates the diffusion of the skin care actives and effectuates their release from the oleaginous composition. It is found surprisingly that by incorporating the release agent into the composition, the skin care actives are more efficiently released to the skin when the compositions exposed to even a small amount of moisture. Not intending to be bound by theory, it is believed that the release agent provides means to microemulsify the composition, and the emulsified composition has a lower viscosity and allows the skin care actives to diffuse more rapidly through the emulsified composition to the surface of the skin. It is also believed that the emulsified composition is more spreadable such that the emulsified composition may deposit a thinner film over the skin surface and render the skin care actives more accessible.

The release agents should also be mild and non-irritating to the skin. It is found that release agents having longer carbon chains are preferred. The long chain molecules tend to coat and form a thin film on the skin surface that do not penetrate into the stratum corneum layer. As such, they are less likely to cause irritations to the skin. They may also function as a protective coating or film on the skin surface that prevents other irritants from direct contact with the skin. Furthermore, since the long chain molecules are relatively wash and sweat resistant, they are long-lasting on the skin surface, thereby enabling a long-lasting and continual delivery of the skin care actives to the skin and achieving greater skin benefits.

In addition, the release agents should preferably have no other undesirable effects on any other structures within the dispensing means. For example, when the dispensing means is an absorbent article, there should be insignificant reduction in web and/or laminate tensile strength, adhesive bond strength, and the like.

The release agents suitable for use herein typically have a HLB value of at least about 3, which include, but are not limited to, nonionic surfactants, polymeric surfactants, and mixtures thereof. The term "HLB" refers to the hydrophilic lipophilic balance. The HLB system is well known in the art and is described in detail in "The HLB System, A Time-Saving Guide to Emulsifier Selection", ICI Americas Inc., August 1984, which is incorporated herein by reference. Nonionic surfactants are preferred because they are comparatively mild and non-irritating to the skin, as opposed to many cationic, anionic or amphoteric surfactants.

Nonlimiting examples of nonionic surfactants useful in the compositions of the present invention are disclosed in McCutcheon's "Detergents and Emulsifiers," North American Edition (1986), published by Allured Publishing Corporation; and McCutcheon's "Functional Materials," North American Edition (1992); both of which are incorporated by reference herein in their entirety.

Nonionic surfactants useful herein include alkoxylated derivatives of the following: fatty alcohols, alkyl phenols, fatty acids, fatty acid esters and fatty acid amides, wherein the alkyl chain is in the C12–C50 range, preferably in the C16–C40 range, more preferably in the C24 to C40 range, and having from about 1 to about 110 alkoxy groups. The alkoxy groups are selected from the group consisting of C2–C6 oxides and their mixtures, with ethylene oxide, propylene oxide, and their mixtures being the preferred alkoxides. The alkyl chain may be linear, branched, saturated, or unsaturated. Of these alkoxylated non-ionic surfactants, the alkoxylated alcohols are preferred, and the ethoxylated alcohols and propoxylated alcohols are more preferred. The alkoxylated alcohols may be used alone or in mixtures thereof. The alkoxylated alcohols may also be used in mixtures with those alkoxylated materials disclosed hereinabove. Commercial materials which may be useful herein as the release agent are available under the tradenames UNITHOX® or PERFORMATHOX® from Petrolite Corp., Polymer Div., Tulsa, Okla.

Other representative examples of such ethoxylate fatty alcohols include laureth-3 (a lauryl ethoxylate having an average degree of ethoxylation of 3), laureth-23 (a lauryl ethoxylate having an average degree of ethoxylation of 23), ceteth-10 (a cetyl alcohol ethoxylate having an average degree of ethoxylation of 10) steareth-10 (a stearyl alcohol ethoxylate having an average degree of ethoxylation of 10), and steareth-2 (a stearyl alcohol ethoxylate having an average degree of ethoxylation of 2), steareth-100 (a stearyl alcohol ethoxylate having an average degree of ethoxylation of 100), beheneth-5 (a behenyl alcohol ethoxylate having an average degree of ethoxylation of 5), beheneth-10 (a behenyl alcohol ethoxylate having an average degree of ethoxylation of 10), and other derivatives and mixtures of the preceding. When employed, these ethoxylated fatty alcohols are typically used in combination with a good barrier protectant, such as petrolatum, at a weight ratio of ethoxylated fatty alcohol to petrolatum of from about 1:1 to about 1:25, preferably from about 1:2 to about 1:15.

Also available commercially are Brij® nonionic surfactants from ICI Specialty Chemicals, Wilmington, Del. Typically, Brij® is the condensation products of aliphatic alcohols with from about 1 to about 54 moles of ethylene oxide, the alkyl chain of the alcohol being typically a linear chain and having from about 8 to about 22 carbon atoms, for example, Brij 72 (i.e., Steareth-2) and Brij 76 (i.e., Steareth-10).

A particularly preferred release agent is a mixture primarily of ethoxylated C20–C40 fatty alcohols having an average molecular weight of the alcohol chain of about 450 and an average degree of ethoxylation of about 10 (available as PERFORMATHOX® 450, from Petrolite Corp.). The long alkyl chain of this molecule gives it better thermal stability and improved miscibility with the oleaginous components of the composition, relative to conventional surfactants having C14–C22 chains typically used in skin care compositions. The long alkyl chain is particularly useful in the manufacture of oil or wax based compositions, which must be heated to a temperature of about 80° C. or higher to melt the oil or wax base and to achieve sufficient mixing with other components. These higher melting PERFORMATHOX materials are also effective in increasing the viscosity of these release compositions such that the compositions are immobilized/retained on or within the dispensing means.

Also useful herein as nonionic surfactants are alkyl glycosides, which are the condensation products of long chain alcohols, e.g. C8–30 alcohols, with sugar or starch polymers. These compounds can be represented by the formula $(S)_n$—O—R wherein S is a sugar moiety such as glucose, fructose, mannose, galactose, and the like; n is an integer of from about 1 to about 1000, and R is a C8–30 alkyl group. Examples of long chain alcohols from which the alkyl group can be derived include decyl alcohol, cetyl alcohol, stearyl alcohol, lauryl alcohol, myristyl alcohol, oleyl alcohol, and the like. Preferred examples of these surfactants are alkyl polyglucosides wherein S is a glucose moiety, R is a C8–20 alkyl group, and n is an integer of from about 1 to about 9. Commercially available examples of these surfactants include decyl polyglucoside (available as APG® 325 CS) and lauryl polyglucoside (available as APG® 600CS and 625 CS), all the above-identified polyglucosides APG® are available from Henkel, Ambler, Pa. Also useful herein are sucrose ester surfactants such as sucrose cocoate and sucrose laurate.

Other nonionic surfactants suitable for use in the present invention are glyceryl esters and polyglyceryl esters, including but not limited to, glyceryl monoesters, preferably glyceryl monoesters of C16–C22 saturated, unsaturated and branched chain fatty acids such as glyceryl oleate, glyceryl monostearate, glyceryl monoisostearate, glyceryl monopalmitate, glyceryl monobehenate, and mixtures thereof, and polyglyceryl esters of C16–C22 saturated, unsaturated and branched chain fatty acids, such as polyglyceryl-4 isostearate, polyglyceryl-3 oleate, polyglyceryl-2 sesquioleate, triglyceryl diisostearate, diglyceryl monooleate, tetraglyceryl monooleate, and mixtures thereof.

Also useful herein as nonionic surfactants are sorbitan esters. Preferable are sorbitan esters of C16–C22 saturated, unsaturated and branched chain fatty acids. Because of the manner in which they are typically manufactured, these sorbitan esters usually comprise mixtures of mono-, di-, tri-, etc. esters. Representative examples of suitable sorbitan esters include sorbitan monooleate (e.g., SPAN® 80), sorbitan sesquioleate (e.g., Arlacel® 83 from ICI Specialty Chemicals, Wilmington, Del.), sorbitan monoisostearate (e.g., CRILL® 6 from Croda, Inc., Parsippany, N.J.), sorbitan stearates (e.g., SPAN® 60), sorbitan triooleate (e.g., SPAN® 85), sorbitan tristearate (e.g., SPAN® 65), sorbitan dipalmitates (e.g., SPAN® 40), and sorbitan isostearate. Sorbitan monoisostearate and sorbitan sesquioleate are particularly preferred emulsifiers for use in the present invention.

Also suitable for use herein are alkoxylated derivatives of glyceryl esters, sorbitan esters, and alkyl polyglycosides, wherein the alkoxy groups is selected from the group consisting of C2–C6 oxides and their mixtures, with ethoxylated or propoxylated derivatives of these materials being the preferred. Nonlimiting examples of commercially available ethoxylated materials include TWEEN® (ethoxylated sorbitan mono-, di- and/or tri-esters of C12 to C18 fatty acids with an average degree of ethoxylation of from about 2 to about 20).

Also useful herein as release agents are polymeric surfactants including but not limited to poloxomers (polyoxyethylene/polyoxypropylene block copolymers) and poloxamines (polyoxyethylene/polyoxypropylene block copolymers of ethylene diamine). These polymeric substances preferably exhibit amphoteric properties in an oleaginous emollient and are capable of at least microemulsifying the composition.

Suitable "poloxomers" comprise block copolymers of polyoxyethylene/polyoxypropylene having the following structure:

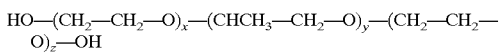

HO—$(CH_2$—$CH_2$—$O)_x$—$(CHCH_3$—$CH_2$—$O)_y$—$(CH_2$—$CH_2$—$O)_z$—OH wherein x has a value ranging from about 2 to about 40, y has a value ranging from about 10 to about 50, and z has a value ranging from about 2 to about 40, and preferably x and z have the same value. These copolymers are available as Pluronic® from BASF Corp., Parsippany, N.J. Suitable poloxamers and poloxamines are available as Synperonic® from ICI Chemicals, Wilmington, Del. or as Tetronic® from BASF Corp., Parsippany, N.J. These polymeric surfactants provide the added benefit of being good barrier protectants.

Other polymeric surfactants useful herein are C12–C22 alkyl-substituted acrylic acid copolymers, wherein the alkyl group is lauric, myristic, palmitic, stearic, behenic, oleic, linolenic isostearic, and mixtures thereof. Nonlimiting examples of the monomeric units for the acrylic acid copolymers include acrylic acids and esters, methacrylic acids and esters, acrylamides, acrylenitriles, and mixtures thereof.

These release agents may be used alone or in combination with other release agents. Total concentration of the release agent will range from about 0.1% to about 60%, preferably from about 0.5% to about 40%, more preferably from 1% to about 20% by weight of the total release composition.

c. Barrier Protectants

A barrier protectant in the release composition topically applied to the skin should be effective for protecting against direct contact between skin and body exudates or other irritants. An effective barrier protectant material spreads easily on the skin surface to provide extensive coverage. As such, it is a physical barrier against moisture and irritants penetration into the skin. It should be long-lasting (i.e., substantive) and mild to the skin. It should preferably be breathable (i.e., vapor permeable but water non-permeable). The barrier protectant also may function as the main carrier medium for the other ingredients in the release compositions of the present invention. The suitable barrier protectants are typically lipophilic and consist of long carbon chains. Generally, the preferred barrier protectant molecules are substantially anhydrous. As used herein, the phrase "substantially anhydrous" means the emollient contains no more than 10%, preferably no more than 5%, more preferably no more than 3% of water. The release composition of the present invention achieves a balance between the moisture-absorbing release agents and the lipophilic barrier protectants for optimal skin benefit, especially for occluded skins.

Moreover, the barrier protectants preferably are long chain, high molecular weight molecules for other advantages, such as long-lasting on the skin surface; non-penetrating hence less irritating to the skin; and higher melting such that they thicken (i.e., increase the viscosity of) the composition to immobilize or retain the composition in the dispensing means when not in use.

Suitable for use herein as barrier protectants are natural waxes such as carnauba, ozokerite, beeswax, candelilla, ceresin, esparto, ouricuri, rezowax; spermaceti, other known mined and mineral waxes; petroleum-derived waxes like paraffin waxes, isoparaffin waxes, and microcrystalline waxes; synthetic waxes, and mixtures of these waxes. Paraffin waxes are typically linear alkanes (i.e., saturated hydrocarbons) having about 16–50 carbons. The most commonly used paraffin wax in skin care compositions is petrolatum (also known as "mineral wax," "petroleum jelly"

and "mineral jelly"). Petrolatum usually refers to the viscous mixtures of hydrocarbons having from 16 to 32 carbon atoms. Paraffin waxes may include isoalkanes and cycloalkanes as well. Isoparaffin waxes are the branched chain version of the linear, saturated hydrocarbons. Microcrystalline waxes typically have an average molecular weight in the range of 500 to 800 (which is about twice that of the paraffin waxes) and more branching than the paraffin waxes. Synthetic waxes are typically polyolefin waxes, such as polyethylene wax and polyethylene/propylene wax (available as Siltex® from Petrolite Corp., Polymers Div., Tulsa Okla.) and polymethylene wax (i.e., Fischer-Tropsch wax). Preferably the wax is a paraffin wax. An example of a particularly paraffin wax is a white petrolatum, available from Witco Corp., Greenwich, Conn., under the tradename Perfecta®.

It is to be understood that some barrier protectants, such as the high melting waxes disclosed above can immobilize or localize the release composition in the dispensing means. In one embodiment, the high melting waxes act to immobilize the release composition on a desired substrate surface such as a web material used in an absorbent article.

Also suitable for use herein as the barrier protectants are C14–C60 fatty alcohols, C14–C60 fatty acids, C14–C60 fatty acid esters, and mixtures thereof. Preferably the alkyl chain of the fatty alcohols, fatty acid, or fatty acid esters is in the C16–C50 range, more preferably in the C24 to C40 range. Representative fatty alcohols include, but are not limited to, cetyl alcohol, stearyl alcohol, behenyl alcohol, and mixtures thereof. When employed, these fatty alcohols are typically used in combination with the petroleum-based barrier protectants, such as petrolatum, at a weight ratio of fatty alcohols to petroleum-based barrier protectants of from about 1:1 to about 1:5, preferably from about 1:1 to about 1:2. Examples of materials that may be useful herein are available under the tradename Unilin®, supplied by Petrolite, Tulsa, Okla., which are mixtures of fatty alcohols and related compounds. Typically, the mixture contain may be 75 to 90% (e.g., 80–85%) of the fatty alcohols, with the balance being substantially all saturated hydrocarbons of corresponding chain length. Examples of fatty alcohol mixtures suitable for use herein include, but not limited to, Unilin® 700, Unilin® 550, Unilin® 425, Unilin® 400, Unilin® 350, Unilin® 325 (all supplied by Petrolite, Tulsa, OK). Examples of suitable fatty acid esters include ester waxes such as stearyl stearate, stearyl behenate, palmityl stearate, stearyl octyldodecanol, cetyl esters, cetearyl behenate, behenyl behenate, ethylene glycol distearate, and ethylene glycol dipalmitate. Examples of commercial ester waxes include Kester® waxes from Koster Keunen, Crodamol® SS from Croda and Demalcare® SPS from Rhone Poulenc.

Other suitable types of barrier protectants for use herein include polysiloxane compounds. In general, suitable polysiloxane materials for use in the present invention include those having monomeric siloxane units of the following structure:

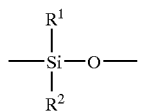

wherein, $R^1$ and $R^2$, for each independent siloxane monomeric unit can each independently be hydrogen or any alkyl, aryl, alkenyl, alkaryl, arakyl, cycloalkyl, halogenated hydrocarbon, or other radical. Any of such radicals can be substituted or unsubstituted. $R^1$ and $R^2$ radicals of any particular monomeric unit may differ from the corresponding functionalities of the next adjoining monomeric unit. Additionally, the polysiloxane can be either a straight chain, a branched chain or have a cyclic structure. The radicals $R^1$ and $R^2$ can additionally independently be other silaceous functionalities such as, but not limited to siloxanes, polysiloxanes, silanes, and polysilanes. The radicals $R^1$ and $R^2$ may contain any of a variety of organic functionalities including, for example, alcohol, carboxylic acid, phenyl, and amine functionalities.

Exemplary alkyl radicals are methyl, ethyl, propyl, butyl, pentyl, hexyl, octyl, decyl, octadecyl, and the like. Exemplary alkenyl radicals are vinyl, allyl, and the like. Exemplary aryl radicals are phenyl, diphenyl, naphthyl, and the like. Exemplary alkaryl radicals are toyl, xylyl, ethylphenyl, and the like. Exemplary aralkyl radicals are benzyl, alpha-phenylethyl, betaphenylethyl, alpha-phenylbutyl, and the like. Exemplary cycloalkyl radicals are cyclobutyl, cyclopentyl, cyclohexyl, and the like. Exemplary halogenated hydrocarbon radicals are chloromethyl, bromoethyl, tetrafluorethyl, fluorethyl, trifluorethyl, trifluorotloyl, hexafluoroxylyl, and the like.

Viscosity of polysiloxanes useful for the present invention may vary as widely as the viscosity of polysiloxanes in general vary, so long as the polysiloxane is flowable or can be made to be flowable for application to the absorbent article. This includes, but is not limited to, viscosity as low as 5 centistokes (at 37° C. as measured by a glass viscometer) to about 20,000,000 centistokes. Preferably the polysiloxanes have a viscosity at 37° C. ranging from about 5 to about 5,000 centistokes, more preferably from about 5 to about 2,000 centistokes, most preferably from about 100 to about 1000 centistokes. High viscosity polysiloxanes which themselves are resistant to flowing can be effectively deposited upon the absorbent articles by such methods as, for example, emulsifying the polysiloxane in surfactant or providing the polysiloxane in solution with the aid of a solvent, such as hexane, listed for exemplary purposes only. Particular methods for applying polysiloxane emollients to absorbent articles are discussed in more detail hereinafter.

Preferred polysiloxanes compounds for use in the present invention are disclosed in U.S. Pat. No. 5,059,282 (Ampulski et al), issued Oct. 22, 1991, which is incorporated herein by reference. Particularly preferred polysiloxane compounds for use as emollients in the compositions of the present invention include dimethicone, phenyl-functional polymethylsiloxane compounds (e.g., Dow Corning 556 Cosmetic-Grade Fluid: polyphenylmethylsiloxane) and cetyl or stearyl functionalized dimethicones such as Dow 2502 and Dow 2503 polysiloxane liquids, respectively. In addition to such substitution with phenyl-functional or alkyl groups, effective substitution may be made with amino, carboxyl, hydroxyl, ether, polyether, aldehyde, ketone, amide, ester, and thiol groups. Of these effective substituent groups, the family of groups comprising phenyl, amino, alkyl, carboxyl, and hydroxyl groups are more preferred than the others; and phenyl-functional groups are most preferred.

Also preferred for use herein are polydialkylsiloxanes, polydiarylsiloxanes, and polyalkylarylsiloxanes, particularly the non-volatile type. These silicones are commercially available from Dow Corning Corporation. These silicones are also disclosed in U.S. Patent No. 5,069,897 issued Dec. 3, 1991, to Orr, and U.S. Pat. No. 5,665,364, issued Sep. 9, 1997, to McAtee et al., the disclosure of both are incorporated herein by reference.

Animal oils and hydrogenated animal oils and waxes are also useful herein as barrier protectants. Nonlimiting examples include, lanolin and derivatives thereof, such as acetylated lanolin (available as Acylan® from Croda Inc., Parsippany, N.J.), and hydrogenated lanolin. Also useful herein are shark liver oil, cod liver oil, and the like. These materials (except lanolin derivatives) are listed in the U.S. Food and Drug Administration's Monographed Materials List, and are generally considered safe for topical applications.

The amount of barrier protectant that can be included in the composition will depend on a variety of factors, including the barrier protectant material used, the other components in the composition, the hardness or viscosity of the composition desired, and like factors. Typically, the composition will comprise from about 1 to about 95%, preferably from about 5 to about 80%, more preferably from about 10 to about 60% and most preferably from about 40 to about 75% by weight of the composition, of the emollient.

d. The Emollients

The composition of the present invention may optionally comprise emollients. Some of the barrier protectants and/or the release agents may have high molecular weights or high melting/softening temperatures, the resultant release composition may not exhibit the optimal rheological properties. Specifically, these release composition may not be readily transferable, i.e., fail to transfer an effective amount of the composition to the skin or satisfactory transfer may require excessive force and/or prolonged contact with skin surface to warm up the composition. It is found that emollients, especially the low melting or low viscosity ones, can be successfully blended with the other components to achieve the desired rheological properties for transfer ability to the skin and immobilization/retention within the dispensing means.

As used herein, the term "emollient" is a material that protects against wetness or irritation, softens, soothes, supples, coats, lubricates, moisturizes, protects and/or cleanses the skin. In addition to providing skin protection and/or therapeutic benefits, emollients may act as the main carrier for other components of the present invention. Emollients useful herein include compositions that are in the form of heat, lotions, creams, oils, ointments, powders, foams, or gels and the like, and may contain any ingredients commonly used in the art for such compositions.

In a preferred embodiment, these emollients will have either a plastic or liquid (i.e., substantially flowable) consistency at ambient temperatures, i.e., 20° C. Suitable emollient may be substantially anhydrous, i.e., having a water content of no more than 5 wt % of the emollient.

Representative emollients useful in the present invention include, but are not limited to, emollients that are petroleum-based emollients; polyolpolyesters; humectants; fatty acid esters; vegetable oils, hydrogenated vegetable oils and waxes; fatty alcohol ethers, particularly those having from 12 to 28 carbon atoms in their fatty chain, such as stearic (C18) chain; other fatty esters of polyhydroxy alcohols, such as mono-, di- and tri-glycerides; any of the monographed skin care actives listed hereinafter; or mixtures of these emollients.

Suitable petroleum-based emollients include those hydrocarbons, or mixtures of hydrocarbons, having chain lengths of from 10 to 32 carbon atoms, not including the longer chain hydrocarbons which are waxy (i.e., at least semi-sold) at room temperature and may also be used as barrier protectants. A particular useful example of petroleum based hydrocarbons having these chain lengths is mineral oil (also known as "liquid petrolatum"). Mineral oil is a mixture of various liquid hydrocarbons obtained by distilling the high boiling (i.e., 300–390° C.) fractions in petroleum. Mineral oil is liquid at ambient temperatures, e.g., 20–25° C. Mineral oil usually refers to less viscous mixtures of hydrocarbons having from 16 to 20 carbon atoms.

Suitable fatty acid ester type emollients include those derived from $C_{12}$–$C_{28}$ fatty acids, preferably $C_8$–$C_{22}$ saturated fatty acids, and short chain ($C_1$–$C_8$, preferably $C_1$–$C_3$) monohydric alcohols. Representative examples of such esters include methyl palmitate, methyl stearate, isopropyl laurate, isopropyl myristate, isopropyl palmitate, ethylhexyl palmitate and mixtures thereof. Suitable fatty acid ester emollients can also be derived from esters of longer chain fatty alcohols ($C_{12}$–$C_{28}$, preferably $C_{12}$–$C_{16}$) and shorter chain acids e.g., lactic acid, such as lauryl lactate and cetyl lactate.

Suitable fatty ester type emollients also include polyolpolyesters as described in U.S. Pat. No. 5,609,587, issued to Roe on Mar. 11, 1997, the disclosure of which is incorporated herein by reference. Exemplary polyols include, but are not limited to, polyhydric compounds such as pentaerythritol; sugars such as raffinose, maltodextrose, galactose, sucrose, glucose, xylose, fructose, maltose, lactose, mannose and crythrose; and sugar alcohols such as erythritol, xylitol, malitol, mannitol and sorbitol. Such polyols are esterified with fatty acids and/or other organic radicals having at least two carbon atoms and up to 30 carbon atoms. While it is not necessary that all of the hydroxyl groups of the polyol be esterified, preferred polyolpolyester emollients of the present invention have substantially all (e.g., at least about 85%) of the hydroxyl groups esterified. Particularly preferred are sucrose polyolpolyesters such as sucrose polycottonate, sucrose polysoyate, and sucrose polybehenate. Mixtures of such polyolpolyesters are also suitable emollients for the present invention. Other suitable polyol polyesters are disclosed in U.S. Pat. No. 5,609,587, issued to Roe on Mar. 11, 1997, and in U.S. Pat. No. 5,607,760, issued to Roe on Mar. 4, 1997, the disclosure of each is incorporated herein by reference. Other ester materials are further described in U.S. Pat. No. 2,831,854, U.S. Pat. No. 4,005,196, to Jandacek, issued Jan. 25, 1977; U.S. Pat. No. 4,005,195, to Jandacek, issued Jan. 25, 1977, U.S. Pat. No. 5,306,516, to Letton et al., issued April 26, 1994; U.S. Pat. No. 5,306,515, to Letton et al., issued Apr. 26, 1994; U.S. Pat. No. 5,305,514, to Letton et al., issued Apr. 26, 1994; U.S. Pat. No. 4,797,300, to Jandacek et al., issued Jan. 10, 1989; U.S. Pat. No. 3,963,699, to Rizzi et al, issued Jun. 15, 1976; U.S. Pat. No. 4,518,772, to Volpenhein, issued May 21, 1985; and U.S. Pat. No. 4,517,360, to Volpenhein, issued May 21, 1985; all of which are incorporated by reference herein in their entirety.

Vegetable oils and hydrogenated vegetable oils and waxes are also useful herein. Some of the fully or partially hydrogenated vegetable oils may be solid or semi-solid (i.e., having a waxy consistency) at ambient temperature. Non-limiting examples of vegetable oils and hydrogenated vegetable oils and waxes include safflower oil, castor oil, coconut oil, cottonseed oil, menhaden oil, palm kernel oil, palm oil, peanut oil, soybean oil, rapeseed oil, linseed oil, rice bran oil, pine oil, sesame oil, sunflower seed oil, jojoba oil, tea tree oil, avocado oil, olive oil, canola oil, their hydrogenated products, cocoa butter, shea butter, and mixtures thereof.

Depending on the skin condition to be treated, humectants may be included in the skin care compositions. A humectant is a type of moisturizing emollient which attracts moisture from the surrounding atmosphere and enhances water absorption of the stratum corneum (i.e., the outer, corny layer of the skin). Nonlimiting examples of humectants useful herein include glycerin and derivatives thereof, such as glycerides, including monoglycerides, diglycerides, triglycerides and mixtures thereof, acetoglycerides, and ethoxylated glycerides of C12–C28 fatty acids; C2–C6 glycols, such as ethylene glycol, propylene glycol, butylene glycol, hexalene glycol, and derivatives thereof, polyethylene glycols (PEGs), such as PEG-2, PEG-3, PEG-30, and PEG-50; polypropylene glycols (PPGs), such as PPG-9, PPG-12, PPG-15, PPG-17, PPG-20, PPG-26, PPG-30, and PPG-34; glycolic esters and ethers, such as C4–C20 alkylether of PEG or PPG, C1–C20 carboxylic acid esters of PEG or PPG, di-C8–C30 alkyl ethers of PEG or PPG; sorbitols and sorbitol esters, trihydroxystearin; triethylene glycol and derivatives; polyhydric alcohols; other ethoxylated derivatives of lipids; and the like.

When present, the amount of emollient that can be included in the composition will depend on a variety of factors, including the particular emollient involved, the skin benefits desired, the other components in the composition, the desired hardness or viscosity of the composition, and like factors. It is preferred that the emollient has a lower melting temperature or a lower viscosity or hardness at ambient temperature than that of the barrier protectant such that the optional emollient(s) are incorporated to achieve a final composition which is a semi-solid or solid for transferability and immobilization/retainability. Typically, the composition will comprise from about 1 to about 95%, preferably from about 5 to about 80%, more preferably from about 10 to about 60% and most preferably from about 30 to about 75% by weight of the composition, of the emollient.

e. Optional Other Components

The compositions can comprise other components typically present in emulsions, creams, ointment, lotions, suspensions, etc. of this type. These components include water, other surfactants, emulsifiers other than skin care agents (i.e., non-water-soluble ones), humectants, skin soothing agents, anti-oxidants, viscosity modifiers, suspending agents, preservatives, sequestering agents, anti-irritants, pH buffering systems, disinfectants, antibacterial actives, antiviral agents, antifungal agents, vitamins, pharmaceutical actives, film formers, perfumes, soothing agents, pigments, deodorants, opacifiers, astringents, colorants, solvents, preservatives, and the like. All of these materials are well known in the art as additives for such compositions and can be employed in appropriate amounts in the compositions for use herein.

Other skin care active ingredients having limited water solubility (i.e., a water solubility of less than 0.1 gram per 100 grams of water) may also be incorporated in the skin care composition for use herein. Such materials include Monographed materials that are deemed safe for use on human skin by the U.S. Food and Drug Administration (FDA) under 21 C.F.R. §347, such as talc, topical starch, zinc oxide, zinc acetate, zinc carbonate, and the like, kaolin, live yeast cell derivatives, microporous cellulose, cholecalciferol, colloidal oatmeal, Peruvean balsam oil, protein hydrlysate, racemic methionine, Vitamin A, and the like, and sodium bicarbonate (which is water soluble). These materials are known to provide multiple skin benefits, such as skin protectant, itch prevention, irritation prevention, via various mechanisms. It will be recognized that several of the these materials are also considered "barrier protectants" as defined herein. Other limited or non-water soluble skin care actives may include, but are not limited to, skin soothing agents derived from botanical extracts, marine sources, mineral sources, and the like, such as aloe vera, chamomile, calendula, comfrey, yarrow, witch hazel, sea weed extract, and oats.

Suitable rheological agents such as suspending agents or viscosity modifiers, may be need for dispersing and suspending the skin care agents in the compositions. Some of the suspending agents may also function as viscosity enhancing agents. Nonlimiting examples of the suspending agents include treated and untreated silicas (e.g., CAB-O-SIL®, available from Cabot Corp., Tuscola, Ill.), organoclays (e.g., BENTONE®, available from Rheox Inc., Hightstown, N.J.), derivatives of castor oil, metal fatty acid soaps, silicates of calcium, magnesium, magnesium/aluminum, and mixtures thereof, talc, cellulose and modified cellulose, polymeric thickeners, certain anionic surfactants, and the like. Particularly preferred suspending agents are disclosed in co-pending U.S. patent application Ser. No. 09/316,691, now abandoned, filed by Gatto et al, on May 21, 1999, the disclosure of which is herein incorporated by reference.

A preservative will also be needed to prevent bacterial growth and odors thereof, particularly in water-based skin care compositions. Suitable preservatives include propyl paraben, methyl paraben, benzyl alcohol, benzalkonium chloride, triclosan, tribasic calcium phosphate, β-hydroxy terephthalate (BHT), or acids such as citric, tartaric, maleic, lactic, malic, benzoic, salicylic, and the like.

Suitable solvents include propylene glycol, glycerine, cyclomethicone, polyethylene glycols, hexalene glycol, diol and multi-hydroxy based solvents.

Suitable vitamins include A, $D_3$, E and derivatives, such as E acetate.

2. The Dispensing Means

The release compositions of the present invention may be applied by hand and/or releasably incorporated into any dispensing means readily apparent to those skilled in the art that directly or indirectly facilitates the transfer of the release composition, particularly the skin care active, to the skin to protect against irritation due to urine, feces and the like. Exemplary dispensing means include, a web material or a substrate such as a tissue, a wipe, a sponge, a cotton ball, a pad, a non-woven, a patch, a bandage, paper, fabric, and the like. The dispensing means may also be a canister, a stick, or a stick casing, an aerosol dispenser, a roller, a pump spray, a trigger spray, and the like. Any combination of the above is also suitable for use herein as a dispensing means. Nonlimiting examples of such delivery vehicles are described in co-pending U.S. patent application Ser. No. 09/326,149, filed by McOsker et al. on Jun. 4, 1999, U.S. patent application Ser. No. 09/370,396, filed by McOsker et al. on Aug. 6, 1999, and U.S. Pat. No. 5,000,356, issued to Johnson et al. on Mar. 19, 1991; all are incorporated herein by reference.

In one embodiment, the dispensing means is one or more components of an absorbent article having the release composition disposed on at least a portion thereof. The component of an absorbent article includes, but is not limited to, the topsheet, the backsheet, any secondary layer(s) intermediate the core and sheet layers, a leg cuff, a side panel, a waist region, an insertable element inserted into the absorbent article for use during wear of the article, specialized structures such as those employed to contain bowel movements (e.g., bowel movement "pockets"), and the like. Preferably the dispensing means is positioned in proximity to the wearer's skin and, more preferably is a component having a wearer-contacting surface such as the topsheet, side panels, leg cuffs, waist region, and the like. Detailed description of suitable absorbent articles and components thereof is disclosed in co-pending U.S. patent application Ser. No. 09/407,950, filed Sep. 28, 1999, U.S. Pat. No. 6,153,209, by Vega et al., the disclosure of which is incorporated herein by reference. Exemplary absorbent articles such as diapers are disclosed in U.S. Pat. No. 3,860,003 issued to Buell on Jan. 14, 1975; U.S. Pat. No. 5,151,092 issued to Buell et al. on Sep. 29, 1992; U.S. Pat. No. 5,221,274 issued to Buell et al. on Jun. 22, 1993; U.S. Pat. No. 5,554,145 issued to Roe et al. on Sep. 10, 1996; U.S. Pat. No. 5,569,234 issued to Buell et al. on Oct. 29, 1996; U.S. Pat. No. 5,580,411 issued to Nease et al. on Dec. 3, 1996; and U.S. patent application Ser. No. 08/915,471, U.S. Pat. No. 6,004,306, entitled "Absorbent Article With Multi-Directional Extensible Side Panels" filed Aug. 20, 1997 in the name of Roble et al. Each of these patents is incorporated herein by reference. Exemplary training pants are disclosed in U.S. Pat. No. 5,246,433, issued to Hasse, et al. on Sep. 21, 1993, U.S. Pat. No. 5,569,234, issued to Buell et al. on Oct. 29, 1996, U.S. Pat. No. 4,940,464, issued to Van Gompel et al. on Jul. 10, 1990 and U.S. Pat. No. 5,092,861, issued to Nomura et al. on Mar. 3, 1992, the disclosure of each of which is incorporated herein by reference. Exemplary feminine hygiene articles are disclosed in U.S. Pat. No. 4,556,146, issued to Swanson et al. on Dec. 3, 1985, U.S. Pat. No. 4,589,876, issued to Van Tilberg on Apr. 27, 1993, U.S. Pat. No. 4,687,478, issued to Van Tilburg on Aug. 18, 1997, U.S. Pat. No. 4,950,264, issued to Osbom, III on Aug. 21, 1990, U.S. Pat. No. 5,009,653, issued to Osborn, III on Apr. 23, 1991, U.S. Pat. No. 5,267,992, issued to Van Tilburg on Dec. 7, 1993, U.S. Pat. No. 5,389,094, issued to Lavash et al. on Feb. 14, 1995, U.S. Pat. No. 5,413,568, issued to Roach et al. on May 9, 1995, U.S. Pat. No. 5,460,623, issued to Emenaker et al. on Oct. 24, 1995, U.S. Pat. No. 5,489,283, issued Van Tilburg on Feb. 6, 1996, U.S. Pat. No. 5,569,231, issued to Emenaker et al. on Oct. 29, 1996, and U.S. Pat. No. 5,620,430, issued to Bamber on Apr. 15, 1997, the disclosure of each of which is incorporated by reference herein. Exemplary incontinence articles are disclosed in U.S. Pat. No. 4,253,461 issued to Strickland, et al. on Mar. 3, 1981; U.S. Pat. Nos. 4,597,760 and 4,597,761 issued to Buell; the above-mentioned U.S. Pat. No. 4,704,115; U.S. Pat. No. 4,909,802 issued to Ahr, et al.; U.S. Pat. No. 4,964,860 issued to Gipson, et al. on Oct. 23, 1990; and in U.S. Pat. No. 5,304,161 issued Apr. 19, 1994 to Noel, et al., the disclosure of each of these references is incorporated herein. Exemplary apertured formed film preferred in feminine hygiene articles are disclosed in U.S. Pat. No. 3,929,135 (Thompson), issued Dec. 30, 1975; U.S. Pat. No. 4,324,246 (Mullane, et al.), issued Apr. 13, 1982; U.S. Pat. No. 4,342,314 (Radel. et al.), issued Aug. 3, 1982; U.S. Pat. No. 4,463,045 (Ahr et al.), issued Jul. 31, 1984; U.S. Pat. No. 5,006,394 (Baird), issued Apr. 9, 1991; U.S. Pat. No. 4,609,518 (Curro et al), issue Sep. 2, 1986 and U.S. Pat. No. 4,629,643 (Curro et al), issued Dec. 16, 1986, each is incorporated by reference. Treatment of topsheet material to improve hydrophilicity is disclosed in U.S. Pat. No. 4,988,344 issued to Reising, et al on January 29, 1991; and U.S. Pat. No. 4,988,345 issued to Reising on Jan. 29, 1991; each of which is incorporated by reference herein. Exemplary elasticized leg cuffs, waist feature, and side panels are disclosed in U.S. Pat. No. 3,860,003; U.S. Pat. No. 4,909,803, issued to Aziz et al. on Mar. 20, 1990; U.S. Pat. No. 4,695,278, issued to Lawson on Sep. 22, 1987; and U.S. Pat. No. 4,795,454, issued to Dragoo on Jan. 3, 1989; in U.S. Pat. No. 4,515,595 issued to Kievit et al. on May 7, 1985; U.S. Pat. No. 5,026,364 issued to Robertson on Jun. 25, 1991; and the above referenced U.S. Pat. No. 5,151,092 issued to Buell et al. on Sept. 29, 1992; U.S. Pat. No. 4,857,067, issued to Wood, et al. on Aug. 15, 1989; U.S. Pat. No. 4,381,781, issued to Sciaraffa, et al. on May 3, 1983; U.S. Pat. No. 4,938,753, issued to Van Gompel, et al. on Jul. 3, 1990; and U.S. Pat. No. 5,151,092, issued to Buell et al. on Sep. 29, 1992; each being incorporated herein by reference.

In another embodiment, the dispensing means is a foam pad which is at least partially filled with the release composition of the present invention. The foam pad and the method of using such dispensing means are described in detail in co-pending U.S. patent application Ser. No. 09/370,396, filed Aug. 6, 1999 by McOsker et al., the disclosure of which is incorporated herein by reference.

Other nonlimiting examples of dispensing means suitable for use herein include: pressure-rupturable or dissolvable microcapsules that are induced to express the skin care active or skin care active composition upon dissolving due to contact with moisture from urine, feces, and the like or rupturing due to pressure from the body or manual rupturing by a user prior to applying the article to a wearer. Examples of pressure-rupturable microcapsules suitable for containing the skin care active are described in U.S. Pat. No. 3,585,998. Such microcapsules may be present in any portion of the absorbent article, including the topsheet. In another example, a water-soluble film that encloses and expresses a powder upon contact with moisture is described in U.S. Pat. No. 4,790,836 and would be a suitable material for use in microcapsules containing the skin care active in any form such as a powder, particulate, liquid or semi-solid. U.S. Pat. No. 4,623,339 describes an insertable layer that is removable from an absorbent article prior to use and manually pressure activatable to express a substance through slits in the layer. The disclosures of each of the foregoing patents are hereby incorporated by reference.

3. Methods of Manufacture

The release composition of the present invention may be manufactured by combining and mixing all the components, including skin care actives, release agents, barrier protectants, and optionally the emollients and other components, such as rheological agents, using techniques generally known in the art. It is to be understood that the components may be combined simultaneously or sequentially, for example, when heat sensitive components are used. Heating the composition to a temperature at least above the softening or melting temperature of the highest melting component is preferred so that a uniform dispersion of the components, particularly skin care active particles, can be easily achieved. Typically, the composition is heated to a temperature in the range from about 35° C. to about 150° C., preferably from 40° C. to about 120° C., more preferably from about 60° C. to about 100° C., prior to being applied to the article. The skin care active ingredients may be added to the composition prior to or after heating. When the actives are in the form of micronized powders or particles, it may be difficult to break up the agglomeration and disperse the powders uniformly. A pre-dispersion step using techniques known in the art may be employed, and the actives in the predispersant are then easily incorporated into the composition. Suitable predispersants may be water, water-miscible solvents, and their mixtures. Dispersing aids or wetting agents known in the art may also be incorporated. Special care should be taken when heat-sensitive ingredients are used, for example, protease inhibitors or enzyme inhibitors. If they are added prior to heating, the composition should be heated to a carefully selected temperature so as not to denature the inhibitors. Alternatively, the inhibitors may be added to the pre-heated composition when it has cooled to a temperature that does not affect the inhibitors but is still sufficiently fluid for mixing and for being applied to the dispensing means. Once the melt composition has been applied to the dispensing means, it is allowed to cool and solidify. Preferably, the application process is designed to aid in the cooling/set-up of the composition such that in substantial amount of agglomeration, stratification or separation of components occur during the cooling/set-up step.

The release composition of the present invention is incorporated into the dispensing means such that it would not interfere with the normal function of the various structures of the dispensing means (e.g., the absorbency of the core, the liquid perviousness of the topsheet, the tackiness of the adhesive, and the like). The dispensing means may contain and/or deliver the skin care active ingredient in any form, such as its neat form, including powder, flake or particulate form, or in the form of a solution, suspension, dispersion, emulsion or the like in a pharmaceutically and idermatologically acceptable carrier.

In one embodiment, the release composition may be incorporated directly onto the surface of or within the material or structure of any type of topsheet, including woven, nonwoven and apertured structured topsheets, the backsheet, and/or absorbent core materials, or other components of an absorbent article during manufacture or assembly by methods which will be readily apparent to those skilled in the art. For example, the release composition can be applied, to the skin contacting surface of an absorbent article or components thereof, such as a topsheet, a backsheet, elasticized leg cuffs, an elasticized waist feature, an elasticized side panels, and the like. Similarly, the release composition may be incorporated onto the surface and/or exterior/interior cavity of other dispensing means including but not limited to tissues, wipes, sponges, rollers, pads, cotton balls, patches, bandages, fabrics, paper, sheet substrates, canisters, sticks, aerosol dispensers and the like. The release composition may be applied to the surface and/or the exterior/interior cavity of the dispensing means by manufacturing methods including but not limited to contact slot coating, gravure coating, extrusion coating, injection, extrusion, spraying, dipping, printing, soaking or otherwise contacting the selected structural element with the release composition. Among the many other methods that can be employed are graft or radical polymerization, or steam treating of the structural elements in order to bind the release composition by hydrogen bonding that is easily reversed when such surfaces are wetted by body waste to release the release composition. Application of the release composition to the structural component material may be either before or after the material is assembled with other raw materials into a finished absorbent article.

In one embodiment where the dispensing means is an absorbent article, the release composition may be applied nonuniformly to the wearer-contacting surface of the article. By "nonuniform" it is meant that the amount, location, pattern of distribution, etc. of the composition can vary over the wearer-contacting surface, and may further vary over specific regions of the article., the properties of the composition, the materials which constitute the composition, and the like. In general, the composition is applied to at least a portion of the absorbent article in an amount ranging from about 0.05 mg/in$^2$ (0.0078 mg/cm$^2$) to about 100 mg/in$^2$ (15.6 mg/cm$^2$), preferably from about 0.1 mg/in$^2$ (0.016 mg/cm$^2$) to about 50 mg/in$^2$ (7.8 mg/cm$^2$), more preferably from about 1 mg/in$^2$ (0.156 mg/cm$^2$) to about 25 mg/in$^2$ (3.9 mg/cm$^2$). For other dispensing means, the release compositions of the present invention are typically loaded in or onto the dispensing means at such a level that the release compositions comprises from about 0.0001% to about 30%, more preferably from about 0.0001% to about 10%, still more preferably from about 0.001% to about 5%, and especially about 0.001% to about 1% by weight of the dispensing means.

Where the release composition is applied to the skin via an absorbent article, the release composition should preferably have a melting/rheological profile as follows: the composition should preferably be solid or semi-solid at room temperature (i.e., about 20° C.) so that "migration" on the article surface and the adverse effects to the absorbency of the article are minimized; the preferred composition should also be readily transferable to the skin by contact, normal wear motions, body heat, and the like. Therefore, the skin care composition is preferably plastic or fluid at skin temperature (i.e., about 34–36° C.) to facilitate the transfer to the skin, and the preferred composition should have storage stability, typically up to at least about 45° C. More detailed description of the melting/rheological profile for a composition suitable for use with various dispensing means is disclosed in U.S. Pat. No. 5,643,588, issued Jul. 1, 1997 to Roe et al.; co-pending U.S. patent application Ser. No. 09/407,950, filed Sep. 28, 1999 by Vega et al.; U.S. patent application Ser. No. 09/326,149, filed by McOsker et al. on Jun. 4, 1999, U.S. patent application Ser. No. 09/370,396, filed by McOsker et al. on Aug. 6, 1999, and U.S. Pat. No. 5,000,356, issued to Johnson et al. on Mar. 19, 1991; all are incorporated herein by reference.

Because the composition is substantially immobilized on the surface of the treated area, relatively small amounts of composition are needed to transfer from the article to skin and to deliver an effective amount of the active. It is believed that the ability to use low levels to impart the desired skin benefits is due to the fact that the composition is continuously, automatically delivered as articles are worn. Surprisingly, while the topsheet or other components of the absorbent article are treated with the release composition nonuniformly (e.g., microscopic or macroscopic regions where no composition is applied), during wear of the article, the composition is transferred to the wearer even in regions of the skin corresponding to untreated regions within the topsheet or other components. The amount and uniformity of composition transferred to the skin is believed to depend on several factors, including, for example, application pattern of the skin care composition, contact of the wearer's skin to the treated article surface, tackiness of the composition, friction created during wear time between the wearer's skin and the treated region, warmth generated from wearer to enhance the transfer of the composition.

EXAMPLES

The following examples further describe and demonstrate embodiments within the scope of the present invention. The examples are given solely for the purpose of illustration and are not to be construed as limitations of the present invention, as many variations thereof are possible without departing form the spirit and scope of the invention.

Example 1

The following is an example of a release composition representative of the present invention. The compositions are formed by combining and mixing the components using technology known in the art.

| Components | Weight % |
| --- | --- |
| Hexamidine Diisethionate | 0.1 |
| Beheneath-10 | 6.3 |
| Petrolatum | 72.6 |
| Behenyl Alcohol | 17.7 |
| Fumed Silica | 3.3 | wherein hexamidine diisethionate is available from Laboratories Serobiologiques, Pulnoy, France; beheneath-10 is available as Mergital® B-10, and behenyl alcohol is available as Lanette®22, both from Henkel Corp., Ambler, Pa.; petrolatum is available as Perfecta® is available from Witco Corp., Greenwich, Conn.; and fumed silica is available as Cab-O-Sil® TS-720 from Cabot, Tuscola, Ill.

Example 2

The following is an example of a release composition representative of the present invention. The compositions are formed by combining and mixing the components using (technology known in the art.

| Components | Weight % |
| --- | --- |
| Hexamidine Diisethionate | 1 |
| Petrolatum | 40 |
| Performathox ® 450 | 59 | wherein hexamidine diisethionate is available from Laboratories Serobiologiques, Pulnoy, France; petrolatum is available as Perfecta® is available from Witco Corp., Greenwich, Conn.; and Performathox® 450 is available from New Phase Technologies, Piscataway, N.J.

Example 3

The following is an example of a release composition representative of the present invention. The compositions are formed by combining and mixing the components using technology known in the art.

| Components | Weight % |
| --- | --- |
| Hexamidine Diisethionate | 1 |
| Petrolatum | 51 |
| Stearyl Alcohol | 35.5 |
| Pluronics ® L43 | 10 |
| Water | 2.5 | wherein hexamidine diisethionate is available from Laboratories Serobiologiques, Pulnoy, France; petrolatum is available as Perfecta® is available from Witco Corp., Greenwich, Conn.; stearyl alcohol is available as CO1879 from The Procter & Gamble Co., Cincinnati, Ohio; and Pluronics® L43 is available from BASF, Piscataway, N.J.

Example 4

Preparation of a Treated Absorbent Article Having a Release Composition Disposed Thereon The release composition example described above is formed by combining and mixing the ingredients using technology known in the art, then deposited on the topsheet of an absorbent article via a contact slot coater, for example, a hot melt adhesive applicator head having multiple slots (Meltex EP11, available from Nordson Corp., Atlanta, Ga.) is suitable for use in the present invention. The composition is placed into a heated tank operating at a temperature of about 77° C. (i.e., about 170° F.). The composition is subsequently applied with a contact applicator onto the topsheet and/or cuffs of a desired article in a striped pattern where the stripes run in the article's longitudinal direction. Specifically, 5 stripes are applied, each stripe measuring about 0.25 inch in width (i.e., the substrate's lateral direction), about 11.7 inches in the longitudinal direction of the substrate, and at an add-on level of about 15.5 mg/in$^2$ (2.4 mg/cm$^2$). The distance between the stripes is about 0.31 inch.

Example 5

Method of Improving the Skin Condition

A person having a need to constant use of an absorbent article, such as an infant, a menstruating female, or an incontinence person, uses an absorbent article having the release composition disposed thereon for a period of at least about 4 days. The subject's article is changed according to routine practice of the user or the caregiver. An unused lotioned article is applied at every change or intermittently with sufficient frequency so as to maintain a small amount of the release composition on the skin. The active is released from the composition while the article is in contact with the subject's skin. The release is enhanced by exposing the composition to moisture in the surrounding. No other intervention, such as skin protective, moisture repellent, and/or pharmaceutical products, is applied to the skin during this period. At the end of the 4 day period, the skin in the general area contacted by the lotion-treated portion of the article shows visible improvement, such as reduction in redness.

The disclosures of all patents, patent applications (and any patents which issue thereon, as well as any corresponding published foreign patent applications), and publications mentioned throughout this description are hereby incorporated by reference herein. It is expressly not admitted, however, that any of the documents incorporated by reference herein teach or disclose the present invention.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. An article, comprising:
   a. a dispensing means: and
   b. a release composition applied to at least a portion of the dispensing means, the release composition comprising:
      (1) from about $10^{-4}$% to about 20%, by weight of the release composition, of at least one skin care active that is selected from the group consisting of hexamidine and its salts and derivatives, triacetin, phytic acid, ethylenediamine tetraacetic acid, phenylsulfonyl fluorides, Vitamins $B_3$, $B_5$, niacinamide, panthenol, Vitamin C and derivatives, chitosan, and mixtures thereof;
      (2) from about 0.1% to about 60%, by weight of the release composition, of a release agent; and (3) from about 0.1% to about 95%, by weight of the release composition, of a barrier protectant;
wherein the dispensing means is selected from the group consisting of a web substrate, an absorbent article, a tissue, a wipe, a sponge, a cotton ball, a pad, a non-woven substrate, a patch, a bandage, paper, fabric;
wherein the release composition is substantially oleaginous and is at least partially transferable to a wearer's skin; and,
wherein the release agent is substantially hydrophilic and oleophilic, has an HLB value of at least about 3 and consists essentially of an ethoxylated C20–C40 fatty alcohol having an average molecular weight of the alcohol chain of at least about 450.

2. The article of claim 1 wherein the dispensing means comprises an absorbent article.

3. The article of claim 1 wherein the portion of a dispensing means is selected from the group consisting of a topsheet, a cuff, a side panel, a waist region, a secondary layer underlying a topsheet, a bowel movement pocket, an insertable element inserted into the absorbent article for use during wear, and combinations thereof.

4. The article of claim 2 wherein the absorbent article is a chassis, the chassis comprising:
a backsheet;
a topsheet joined to the backsheet:
an absorbent core positioned between the topsheet and the backsheet; and
a cuff joined to the chassis.

5. The article of claim 1 wherein the skin care active has a water solubility of at least 0.1 gram of skis care active per 100 grams of water at 25° C.

6. The article of claim 1 wherein the barrier protectant is selected from the group consisting of C14–C60 fatty alcohols, C14–C60 fatty acids; C14–C60 fatty acid esters; natural waxes; paraffin waxes; synthetic waxes; modified polysiloxanes having alkyl, phenyl or alkylphenyl groups; animal oils and hydrogenated animal oils and waxes; and mixtures thereof.

7. The article of claim 1 further comprising optional ingredients selected from the group consisting of petroleum based emollients, polyolpolyester, fatty acid ester emollients, vegetable oils, hydrogenated vegetable oils and waxes, humectants, fatty alcohol ethers, talc, topical starch, zinc salts, kaolin, live yeast cell derivatives, microporous cellulose, colloidal oatmeal, cholecalciferol, Peruvean balsam oil, protein hydrlysate, racemic methionine, vitamins, and the like, aloe vera, and mixtures thereof.

8. A method for effectively delivering one or more skin care actives to skin, comprising:
(a) applying to the skin an article comprising a dispensing means and a release composition disposed on at least a portion of the dispensing means;
wherein the release composition is substantially oleaginous and comprises:
(1) from about $10^{-4}$% to about 20%, by weight of the release composition, of at least one skin care active that is selected from the group consisting of hexamidine and its salts and derivatives, triacetin, phytic acid, ethylenediamine tetraacetic acid phenylsulfonyl fluorides, Vitamins $B_3$, $B_5$, niacinamide, panthenol, Vitamin C and derivatives, chitosan, and mixtures thereof;
(2) from about 0.1% to about 60%, by weight of the release composition, of a release agent; and
(3) from about 0.1% to about 95%, by weight of the release composition, of a barrier protectant;
wherein the dispensing means is selected from the group consisting of a web substrate, an absorbent article, a tissue, a wipe, a sponge, a cotton ball, a pad, a non-woven substrate, a patch, a bandage, paper, fabric,
(b) transferring at least a portion of the release composition to the skin;
(c) exposing the release composition, to moisture; and
(d) releasing one or more skin care active ingredients from the release composition; and wherein the release agent is substantially hydrophilic and oleophilic, has an HLB value of at least about 3 and consists essentially of an ethoxylated C20–C40 fatty alcohol having an average molecular weight of the alcohol chain of at least about 450.

9. The method of claim 8 wherein the dispensing means comprises an absorbent article and the portion of the absorbent article is selected from the group consisting of a topsheet, a cuff, a side panel, a waist region, a secondary layer underlying the topsheet, a bowel movement pocket, an insertable element inserted into the dispensing means for use during wear, and combinations thereof.

10. The method of claim 8 wherein the barrier protectant is selected from the group consisting of C14–C60 fatty alcohols; C14–C60 fatty acids; C14–C60 fatty acid esters; natural waxes; paraffin waxes; synthetic waxes; modified polysiloxanes having alkyl, phenyl or alkylphenyl groups; animal oils and hydrogenated animal oils and waxes; and mixtures thereof.

11. The method of claim 8 further comprising optional ingredients selected from the group consisting of petroleum based emollients, polyolpolyester, fatty acid ester emollients, vegetable oils, hydrogenated vegetable oils and waxes, humectants, fatty alcohol ethers, talc, topical starch, zinc salts, kaolin, live yeast cell derivatives, microporous cellulose, colloidal oatmeal, cholecalciferol, Peruvean balsam oil, protein hydrlysate, racemic methionine, vitamins, and the like, aloe vera, and mixtures thereof.

12. A method for improving the skin condition of a wearer in an area covered by a treated absorbent article, comprising:
(a) applying to the wearer an absorbent article, said absorbent article having a release composition applied to at least a portion thereof;
wherein the release composition is substantially oleaginous and comprises:
(1) from about $10^{-4}$% to about 20%, by weight of the release composition, of at least one skin care active that is selected from the group consisting of hexamidine and its salts and derivatives, triacetin, phytic acid, ethylenediamine tetraacetic acid, phenylsulfonyl fluorides, Vitamins $B_3$, $B_5$, niacinamide, panthenol, Vitamin C and derivatives, chitosan, and mixtures thereof;
(2) from about 0.1% to about 60% by weight of the release composition, of a release agent; and
(3) from about 0.1% to about 95% by weight of the release composition, of a barrier protectant and;
wherein the release agent is substantially hydrophilic and oleophilic, has an HLB value of at least about 3 and consists essentially of an ethoxylated C20–C40 fatty alcohol having an average molecular weight of the alcohol chain of at least about 450,
(b) transferring at least a portion of the release composition to the wearer while the article is worn;

(c) exposing the release composition to moisture;
(d) releasing the skin care active ingredient from the release composition; and
(e) repeating steps (a–d) with one or more additional treated absorbent articles with sufficient frequency to improve skin condition in the area covered by the treated absorbent article, relative to skin covered by an untreated absorbent article.

* * * * *

UNITED STATES PATENT AND TRADEMARK OFFICE
CERTIFICATE OF CORRECTION

PATENT NO.    : 6,716,441 B1
DATED         : April 6, 2004
INVENTOR(S)   : Scott Edward Osborne et al.

It is certified that error appears in the above-identified patent and that said Letters Patent is hereby corrected as shown below:

Column 12,
Lines 46 and 61, delete "Dow Coming" and insert therefor -- Dow Corning --.

Column 19,
Line 19, delete "idermatologically" and insert therefor -- dermatologically --.

Signed and Sealed this

Twentieth Day of July, 2004

JON W. DUDAS
*Acting Director of the United States Patent and Trademark Office*